United States Patent
Teng et al.

(10) Patent No.: US 6,531,158 B1
(45) Date of Patent: Mar. 11, 2003

(54) DRUG DELIVERY SYSTEM FOR ENHANCED BIOAVAILABILITY OF HYDROPHOBIC ACTIVE INGREDIENTS

(75) Inventors: Ching-Ling Teng, Fremont, CA (US); Charles Hsiao, Livermore, CA (US); Joshua Gatts, Hayward, CA (US)

(73) Assignee: Impax Laboratories, Inc., Haywood, CA (US)

(*) Notice: Subject to any disclaimer, the term of this patent is extended or adjusted under 35 U.S.C. 154(b) by 36 days.

(21) Appl. No.: 09/635,234

(22) Filed: Aug. 9, 2000

(51) Int. Cl.[7] ............... A61K 9/14; A61K 9/48; A61K 9/20; A61K 9/50; A61K 9/26

(52) U.S. Cl. ............ 424/489; 424/451; 424/464; 424/469; 424/470; 424/489; 424/499

(58) Field of Search .................. 424/451, 464, 424/484, 489, 469, 470, 499

(56) References Cited

U.S. PATENT DOCUMENTS

| | | | |
|---|---|---|---|
| 3,639,637 A | 2/1972 | Campbell | 424/346 |
| 4,013,785 A | 3/1977 | Weintraub et al. | 424/23 |
| 4,344,934 A * | 8/1982 | Martin et al. | 424/80 |
| 4,412,986 A | 11/1983 | Kawata et al. | 424/80 |
| 4,436,743 A | 3/1984 | Schonafinger et al. | 424/269 |
| 4,558,058 A | 12/1985 | Schonafinger et al. | 514/342 |
| 4,629,624 A | 12/1986 | Grouiller et al. | 424/78 |
| 4,721,709 A | 1/1988 | Seth et al. | 514/221 |
| 4,800,079 A | 1/1989 | Boyer | 424/482 |
| 4,859,703 A | 8/1989 | Krause | 514/543 |
| 4,895,726 A * | 1/1990 | Curtet et al. | 424/456 |
| 5,769,934 A | 6/1998 | Ha et al. | 106/162.8 |
| 5,827,536 A | 10/1998 | Laruelle | 424/451 |
| 5,948,438 A | 9/1999 | Staniforth et al. | 424/464 |
| 6,074,670 A * | 6/2000 | Stamm et al. | 424/462 |
| 6,372,790 B1 * | 4/2002 | Bonhomme et al. | 514/555 |

FOREIGN PATENT DOCUMENTS

| | | |
|---|---|---|
| EP | 0 179 583 | 10/1984 |
| EP | 0 239 541 | 9/1987 |
| EP | 0 256 933 | 2/1992 |
| EP | 0 757 911 | 2/1997 |
| WO | WO 82/01649 | 5/1982 |
| WO | WO 87/00428 | 1/1987 |
| WO | 90/04962 | * 5/1990 |

OTHER PUBLICATIONS

Westerberg et al., "Physiochemical Aspects of Drug Release XVII", International Journal of Pharmaceutics (1993); p. 1–17.*

Sheu et al., "Characterization and Dissolution of Fenofibrate Solid Dispersion Systems", International Journal of Pharmaceutics (1994); p. 137–146.*

Darja et al., "Solubilization and Dissolution Enhancement for Sparingly Soluble Fenofibrate", Acta Pharm (1996); p. 131–136.*

Mortada, Lobna M., et al., "Enhancement of Dissolution Rates of Some Water Insoluble Drugs by the Solvent Deposition Technique." *Acta Pharmaceutica Technologica* 28(4) 1982, pp. 297–301.

(List continued on next page.)

Primary Examiner—Thurman K. Page
Assistant Examiner—S. Tran
(74) Attorney, Agent, or Firm—Blank Rome LLP (57) ABSTRACT

The present invention provides a drug delivery system for the oral administration of a hydrophobic active ingredient. The active ingredient's post-ingestion dissolution rate and its corresponding bioavailability can be optimized by intimately mixing a micronized hydrophobic drug with suitably sized inert particles to a dispersion that will facilitate desired bioavailability. In a particular embodiment, the hydrophobic active ingredient is fenofibrate. Suitably sized inert particles include microcrystalline cellulose and lactose. Dispersion may be monitored by microscopic visualization.

19 Claims, 6 Drawing Sheets

OTHER PUBLICATIONS

El–Samaligy, Mohamed S., et al., "Adsorption–desorption effect of microcrystalline cellulose on ampicillin and amoxycillin." *International Journal of Pharmaceutics*, 31 (1986) 137–144.

Sjokvist, E., et al., "Physicochemical aspects of drug release. VI. Drug dissolution rate from solid particulate dispersions and the importance of carrier and drug particle properties." *International Journal of Pharmaceutics*, 47 (1988) 51–66.

te Wierik, G.H.P. et al., "Improvement of dissolution of poorly soluble drugs by solid deposition on a super disintegrant." *Acta Pharm. Nora.* 4(4) 239–244 (1992).

Westerberg, M., et al., "Physicochemical aspects of drug release XVII. The effect of drug surface area coverage to carrier materials on drug dissolution from ordered mixtures." *International Journal of Pharmaceutics*, 90 (1993) 1–17.

Sheu, M–T, et al., "Characterization and dissolution of fenofibrate solid dispersion systems." *International Journal of Pharmaceutics*, 103 (1994) 137–146.

Temeljotov, Darja F., et al., "Solubilization and dissolution enhancement for sparingly soluble fenofibrate." *Acta Pharm.* 46 (1996) 131–136.

Noyes, A. A. and Whitney, W. R., J. Am. Chem. Soc., 19, 930 (1897).

Cooper, B. F. and Brecht, E. A., J. Amer. Pharm. Assoc. Sci. Ed. 46, 520 (1957).

Munzel et al., Galenische Praktikum, Stuttgart 1959, "14.2.2 The formation of a Coating with Insoluble . . . " pp. 374, 412–415.

Wurster, D. and Seitz, J., J. Am. Pharm. Assoc. Sci., Ed., 49, 335 (1960).

Stephenson, D., Pharm. Weekblad. 96, 689 (1961).

Wurster, D. E. and Taylor, P.W., J. Pharm. Sci. 54, 1654 (1965).

Bates, T. R., Gibaldi, M., and Kanig, J. L., Nature 210, 1331 (1966).

Aguair, A. J., Zelmer, J. E. and Kinkel, A. W., J. Pharm. Sci., 56, 1243–1252 (1967).

Feinholt, P. and Solvang, R., J. Pharm. Sci., 57, 1322–1326 (1968).

Pharmacie Galenique, vol. III, New Edition, Liege University, A. Denoel et al., "Solid divisional . . . " 1968.

Lin, S. L., Menig, J. and Lachman, L., J. Pharm. Sci., 57 (1968).

Martin, A. N., Swarbrick, J., Cammarata, A. and Chun, A. H. C., Modern Pharmaceutics, p. 452, Lea and Febiger, Philadelphia, (1969).

Horn, F. and Miskel, J., J. Pharm. Sci. 59, 827 (1970).

Remington's Pharmaceutical Sciences, Fourteenth Edition, 1970, "Pharmaceutical Necessities," Chapter 71, pp. 1316–1348.

Blake, M. J., J. Amer. Pharm. Ass. NS 11, 603 (1971).

Mattok, G. L., McGilveray, 1. J. and Mainville, C. A., J. Pharm. Sci. 60, 561 (1971).

Kaplan, S. A., Drug Metab. Rev. 1, 15 (1972).

Perry, R. H., and Chilton, C. H., Principles of Size Reduction, pp. 8–8 to 8–14, 8–4 to 8–44 in Chemical Engineers' Handbook, McGraw–Hill Book Co., New York (1973).

Johnson, B. F., Greer, H., McCrerie, J. A., Bye, C. and Fowle, A. S., Postgrad. Med. J. 50, 548 (1974).

Sullivan, T. J., Sakmar, E., and Wagner, J. G., J. Pharmacokinetics Biopharm. 4, 173 (1976).

Frazier, W.F. and Nuessler, M. D., J. Pharm. Sci. 65, 1823 (1976).

Crooks, M. J. and Ho, R., Powder Technol. 14, 161 (1976).

Samaligy, M. S. and Szantmiklosi, P., Pharm. Ind. 40, Nr. 3, 274 (1978).

Hoener, B. and Benet, L. Z., Factors Influencing Drug Absorption and Drug Availability, in Modern Pharmaceutics, Banker, G. S. and Rhodes, C. T., Eds., pp. 152–159, Marcel Dekker, N.Y. (1979).

Marshall, K., Solid Oral Dosage Forms, in Modern Pharmaceutics, Banker, G. S. and Rhodes, C. T., Eds., pp. 381–382, Marcel Dekker Inc., New York (1979).

Greene, D. S., Preformulation, in Modern Pharmaceutics, Banker, G. S. and Rhodes, C.T. Eds., pp. 211–225, Marcel Dekker Inc., New York (1979).

Schwartz, J.B., Optimization techniques in Pharmaceutical Formulation and Processing, in Modern Pharmaceutics, Banker, G. S. and Rhodes, C. T. Eds., pp. 711–734, Marcel Dekker, New York (1979).

Banker, G. S., Drug Products: Their Role in the Treatment of Disease, Their Quality, and Their Current and Future Status as Drug Delivery Systems, in Modem Pharmaceutics, Banker, G. S. and Rhodes, C. T. Eds., pp. 16–21, Marcel Dekker, New York (1979).

Physical Chemical Properties of Drugs, 1980, "Solubility and Partitioning in Drug Design," pp. 207–229.

Wadke, D. A. and Jacobson, H., Preformulation Testing in Pharmaceutical Dosage forms: Tablets, vol. 1, Lieberman, H. A. and Lachman, L., pp. 1–56, Marcel Dekker, New York (1980).

Lantz, R. J. and Schwartz, J. B., Mixing, in Pharmaceutical Dosage forms: Tablets, vol. 2, Lieberman, H. A. and Lachman, L., Eds., pp. 22–26, Marcel Dekker Inc., New York (1981).

Holzer, A. E. and Sjogren, J., Acta. Pharm. Sueic. 18, 139 (1981).

Galenica Pharmacy 2 Biopharmacie, $2^{nd}$ Edition, 1982, Chapter 10, Sections 1–5, pp. 591–525.

Galencia 2 Biopharmacie, $2^{nd}$ Edition, 1982, Chapter 4, pp. 151–159 and 335 regarding dissolution.

Lotter, A., Flanagan, D., Palepu, N. and Guillory, K., Pharm. Technol., 7, 32 (1983).

Merck Index, 10, 3914 (1984).

Esezobo, S., J. Pharm. Pharmacop. 37, 193 (1984).

G. Boullay, STP Pharma 1(4), "Microgrinding and dissolution," pp. 296–299. 1985.

Nystrom, C. and Westerman, M., J. Pharm. Phannacol., 3 8, 161–165 (1985).

Boullay, G., S. T. P. Pharma 1(4), 296 (1985).

Parrott, E. L., Milling, in The Theory and practice of Industrial Pharmacy, Lachman, L., Lieberman, H. A. and Kanig, J. L., pp. 44–45, Lea and Febiger, Philadelphia (1986).

Dictionnaire Vidal 63a Edition, 1987, p. 882 containing Lipanthyl® 300.

Wan, L. S. and Heng, P. W., Pharm. Acta Helv. 62, Nr. 5–6, 169 (1987).

Abdou, H. A., Theory of Dissolution, in Dissolution, Bioavailability and Bioequivalence, pp. 11–14, 26–28, 58–70, 80–82, Mack Publishing Co., Easton, PA, (1989).

Remington's Pharmaceutical Sciences, Eighteenth Edition, 1990, "Oral Solid Dosage Forms," Chapter 89, pp. 1633–1639.

Galenique Pharmacy, 6$^{th}$ Edition, 1992, "III—Dissolution," Prof. Y. Cohen, pp. 127–131.

Tools for Structure Activity Relationships User's Guide, 1993, Understanding Tsar.

Vidal 1995, 71e Edition, various pages containing Enantone; Gevatran; Praxilene; Seglor; and Zoladex.

Letter from Lab Service S.A. dated Jul. 30, 1999 from George Boullay.

Giroud et al., Pharmacologie Clinique, "Factors Influencing Biostability," pp. 131–135.

* cited by examiner

DRUG DELIVERY SYSTEM FOR ENHANCED BIOAVAILABILITY OF HYDROPHOBIC ACTIVE INGREDIENTS

FIELD OF THE INVENTION

The present invention provides a drug delivery system for the oral administration of a hydrophobic active ingredient. The active ingredient's post-ingestion dissolution rate and its corresponding bioavailability can be optimized by intimately mixing a micronized hydrophobic drug with suitably sized inert particles to form a dispersion that will facilitate desired bioavailability.

BACKGROUND OF THE INVENTION

Drug efficacy depends upon its bioavailability to the patient. For drugs that are hydrophobic or poorly soluble in water, increased wettability upon exposure to biological fluids can become a goal for those formulating and manufacturing these agents.

For example, the bioavailability of pharmacologically active entities that are hydrophobic may be enhanced by reduction of particle size. See, e.g., Mortada & Mortada 28 (4) Acta Pharm. Tech. 297–301 (1982); U.S. Pat. No. 4,344,934, Martin et al.; WO 90/04962, Nystrom et al. Such micronization of an active principle may improve the dissolution of the active principle in vivo, and thus improve its bioavailability, but the agglomeration of the micronized particles can diminish these characteristics.

Alternatively, the use of a surfactant, such as sodium lauryl sulfate, in a formulation of an active principle may improve absorption of the drug, and hence improve its bioavailability. For example, the co-micronization of an active ingredient with a solid surfactant to improve a water-insoluble drug's in vivo bioavailability has been described. U.S. Pat. No. 4,895,726, Curtet, et al. The present invention minimizes the use of surfactants, thus avoiding possible reactivity or sensitivity to the surfactant.

Microcrystalline cellulose has been used as an excipient in the manufacture of pharmaceuticals. See, e.g., El-Samaligy et al., 31 Int'l J. Pharma. 137–44 (1986). However, it reportedly interfered with the bioavailability, or reduced the activity, of ampicillin and amoxycillin when used as a carrier. Id. On the other hand, microcrystalline cellulose has been mixed with diethylstilbestrol to improve the dispersability of that hydrophobic drug in animal feed. U.S. Pat. No. 3,639,637, Campbell. Microcrystalline cellulose has also been included as an excipient in formulations comprising water-soluble n-acetyl-p-aminophenol and fumed silica. U.S. Pat. No. 4,013,785, Weintraub et al.

In one embodiment, this invention can provide for improved wettability of hydrophobic pharmaceutical agents upon exposure to biological fluids. The inventors of the present invention discovered unexpectedly that the dispersion achieved by intimately mixing a micronized hydrophobic drug with inert particles of suitable size, such as lactose or microcrystalline cellulose, and, optionally, other suitable substrates, increases the dissolution rate of the drug and hence improves its bioavailability. The intimate mixing and maximized dispersion of the micronized drug with a material of small particle size and irregular surface area, such as microcrystalline cellulose or lactose, can separate active agglomerates and disperse them to the substrate surface, resulting in a lower surface tension thereby improving wettability upon exposure to biological fluids.

A capsule formulation, including the carrier particle and hydrophobic active ingredient, may be manufactured by intimately mixing the micronized active ingredient(s) with the suitably sized particles, such as lactose or microcrystalline cellulose, with or without a disintegrant or other excipients, for a period of time sufficient to maximize dispersion of the active ingredient to the carrier. Dispersion may be monitored optically, for example. The granulate mixture is then wetted with an appropriate granulation solution, with or without surfactant or other excipients. After the wet granules are dried, they are milled to desirable granule size. The milled granules may be blended with a suitable lubricant or other non-lubricant excipient. The final blend is then filled into capsules of suitable size.

SUMMARY OF THE INVENTION

An objective of the present invention is a drug delivery system comprising a micronized hydrophobic drug and an inert substrate of suitable particle size. In a particular aspect of the invention, the inert substrate is microcrystalline cellulose. In another aspect of the invention, the inert substrate is lactose. In a preferred embodiment of the invention, the inert substrate has a mean particle size of about 1 micron to 500 microns in size. More preferably, the inert substrate has a mean particle size of less than about 50 microns.

Another object of the invention provides a drug delivery system in which the active ingredient is micronized fenofibrate or an acceptable salt of fenofibrate. In another object of the invention, the drug delivery system includes fenofibrate and an inert substrate of suitable size, such as microcrystalline cellulose or lactose.

In a preferred embodiment of the invention, the ratio of the inert substrate to the hydrophobic drug is between 0.1 and 10.0. More preferably, the ratio of the inert substrate to the hydrophobic drug is between about 0.1 and 4.0. Most preferably, the ratio of the inert substrate to the hydrophobic drug is between about 0.3 and 2.0. In another preferred embodiment, the inert substrate is microcrystalline cellulose. In an alternative preferred embodiment, the inert substrate is lactose.

Another objective of the present invention is a method of improving the bioavailability of a hydrophobic drug, comprising the steps of micronizing said hydrophobic drug and mixing it with an inert substrate of suitable particle size until the drug is optimally dispersed with the inert material.

Still another objective of the present invention provides for a method for treating high cholesterol by administering to a patient in need thereof a pharmaceutical composition comprising fenofibrate and either microcrystalline cellulose or lactose.

The present invention also provides for a method of preparing a pharmaceutical composition with increased bioavailability of a hydrophobic active ingredient, by mixing intimately that active ingredient with an inert substance of suitable particle size until desired dispersion is achieved, wet-granulating the mixture in the presence of solvent, drying the wet granules, milling the dried granules to desirable granule size, blending the milled granules with a lubricant, and filling the milled granules into a capsule of suitable size. In one aspect of this embodiment, the particles are lactose. In another aspect, the particles are microcrystalline cellulose. Another aspect of this embodiment includes adding a disintegrant to the formulation. Another aspect includes adding a surfactant to assist in wetting the mixture.

DETAILED DESCRIPTION

The advantages of the present invention are obtained, e.g., when using hydrophobic pharmaceutical substances that are not readily dissolved in water, although the degree of water solubility can vary with the type of substance used, and the intention is not that the solubility of the active pharmaceutical substance or substances shall constitute a limitation of the invention. One skilled in the art may easily establish, by routine experimentation, whether a pharmaceutical substance can be used in a pharmaceutical composition according to this invention.

Examples of active ingredients that are considered hydrophobic, poorly water-soluble or water-insoluble include benzodiazepines, clofibrate, chlorpheniramine, dinitirate, digoxin, digitoxin, ergotamin tartate, estradiol, fenofibrate, griseofulvin, hydrochlorothiazide, hydrocortisone, isosorbide, medrogeston, oxyphenbutazone, prednisolone, prednisone, polythiazide, progensterone, spironolactone, tolbutamide, 10,11-dihydro-5H-dibenzo[a,d]cyclo-heptene-5-carboxamide; 5H-dibenzo[a,d]cycloheptene-5-carboxamide, fish oil and the like. This recitation is in no way exhaustive.

Many hydrophobic active ingredients are available commercially in micronized form, or may be micronized by methods well known to those skilled in the art. For example, micronized active ingredients may be reduced to a fine powder by use of conventional methods such as an air-jet micronizer. The fenofibrate of the instant invention may be purchased in micronized form.

Inert particles of suitable size, as embodied in the present invention, may be any pharmaceutically acceptable excipient. Water-soluble excipients include, but are not limited to, for example, sugars such as lactose, mannitol, dextrose and sorbitol. Water-insoluble excipients include, but are not limited to, for example, microcrystalline cellulose, calcium phosphate, and many synthetic or organic polymers. Inert substrates that are suitable particles for the present invention are well known in the art. See, e.g., Wade & Waller, Handbook of Pharmaceutical Excipinets ($2^{nd}$ ed. 1994).

In particular, microcrystalline cellulose is a highly crystalline, insoluble, particulate cellulose consisting primarily of crystalline aggregates obtained by removing amorphous (fibrous cellulose) regions of a purified cellulose source material derived from, for example, wood pulp or cotton linters. Various methods for producing microcrystalline cellulose include steam explosion, acid hydrolysis, and pressure treatment. See, e.g., U.S. Pat. No. 5,769,934, Ha et al. Microcrystalline cellulose is considered insoluble.

Another example, the disaccharide sugar lactose, is well known in the art as a water soluble excipient in pharmaceutical preparations. Lactose can be milled to the appropriate minute size by standard methodologies, e.g., passing through a suitably sized screen, or various particle sizes can be obtained commercially.

The size of inert substrate particles preferred in the present invention may range from about 1 micron to 500 microns. Preferably, the inert substrate particles are smaller than about 100 microns in size. Most preferably, the inert substrate particles are less than about 50 microns in size. Particles having irregular surface areas are also preferred. Microcrystalline cellulose is available commercially as, for example, EMCOCEL® from Edward Mendell Co., Inc. (Cedar Rapids, Iowa.) and AVICEL® from FMC BioPolymer. (Philadelphia, Pa.). Lactose is available commercially from numerous sources, such as FMC BioPolymer. It may be milled, e.g., through an appropriately sized mesh screen, to a suitable particle size.

In a preferred embodiment of the invention, the ratio of inert ingredient to active ingredient is between 0.1 to 10.0 weight/weight. More preferably, the ratio of the inert substrate to the hydrophobic drug is between about 0.1 and 4.0. Most preferably, the ratio of the inert substrate to the hydrophobic drug is between about 0.3 and 2.0.

Different types of equipment can be used to achieve the desired degree of dispersion. Dispersion of the active ingredient and the inert particles may be monitored easily by visualization. Accordingly, a sample is removed from the batch being mixed, placed on a microscope slide with water or a very low concentration of surfactant solution, and viewed under magnification. Agglomerates or aggregates of poorly dispersed active ingredient absorb light and appear as opaque bodies. Visualization also provides for standardized and uniform dispersion levels among different batches.

Other methods of monitoring dispersion include scanning electron microscopy which visually presents the degree of dispersion; analyzing the dissolution rate of the preparation; testing the light obscuration particle count; and measuring the wetting time, i.e., timing how long it takes for the powder blend to sink after being placed on a solution surface.

The pharmaceutical compositions produced in accordance with this invention may be used in different types of pharmaceutical preparations. The preparations will preferably be intended for enteral administration, primarily for oral administration. The preparations may be in solid form, for instance, in capsule, powder or granule, or tablet form or in the form of suppositories for rectal administration. Alternatively, the formulation may be dispersed into a suitable liquid for, e.g., pediatric use. Pharmaceutical compositions prepared in accordance with the invention may also be used in preparations for external use, such as in ointments and creams.

The pharmaceutical preparations can be formulated by combining the inventive pharmaceutical compositions with the conventional pharmaceutical additives and excipients, normally used in the desired forms of the preparations, with the aid of known methods. Such additions may comprise, for example, additional carriers, binders, preservatives, lubricants, glidants, disintegrants, flavorants, dyestuffs and like substances, all of which are well known in the art.

The pharmaceutical preparations herein may be prepared by wet granulation. The wet granulation procedure includes mixing the microcrystalline cellulose and the micronized active ingredient to be incorporated into a dosage form with a suitable solvent in, for example, a high shear granulator, twin shell blender or double-cone blender, or a simple planetary mixer, and thereafter adding solutions of a binding agent to the mixed solution to obtain a granulation. Suitable solvents include water, or other polar organic solvents such as alcohols. After mixing, the damp mass, optionally, can be screened through a suitably sized mesh screen, and then dried via, for example, tray drying, the use of a fluid-bed dryer, spray dryer, radio-frequency dryer, microwave, vacuum, or infra-red dryer. A Fitzmill or Co-mill or oscillating mill may be used to control granule size. A V-blender or double cone blender may be used for final blending.

Alternatively, the mixed microcrystalline cellulose/ micronized active agent may be mixed with solvent for wet granulation in the presence of a suitable surfactant. Suitable surfactants may be ionic or nonionic, and are well-known to those practicing the art.

Disintegrants are often added to ensure that the ultimate prepared solid dosage form has an acceptable disintegration rate in the environment of use, such as the gastrointestinal tract. Typical disintegrants include starch derivatives and salts of carboxymethyl cellulose such as croscarmellose.

The milled granule may optionally be blended with a lubricant. Lubricants include magnesium stearate, sodium stearate, magnesium sulfate, steric acid or talc. Such lubricants are commonly included in the final tableted or capsuled product.

Bioavailability refers to the degree to which the therapeutically active medicament becomes available in the body after administration. Typically, bioavailability is measured in patients who fasted overnight before being dosed with the test preparation. Plasma samples are then taken and analyzed for the plasma concentration of the parent compound and/or its active metabolite. These data may be expressed as Cmax, the maximum amount of active ingredient found in the plasma, or as AUC, the area under the plasma concentration time curve. Shargel & Yu, Applied Biopharmaceutics adf Pharmacokinetics ch. 10 (3rd Ed. 1996); see also APPLIED Pharmacokinetics: Principles of Therapeutic Drug Monitoring (Evans et al., eds., 3rd ed. 1992).

It will be appreciated by those skilled in the art that although the invention is illustrated with particularly hydrophobic drugs, the composition and method of this invention is also applicable to more soluble drugs in need of enhanced bioavailability.

Without further elaboration, it is believed that one skilled in the art can, using the preceding description, utilize the present invention to the fullest extent. The following examples are illustrative only, and not limiting of the remainder of the disclosure in any way whatsoever.

EXAMPLES

Example 1

Formulations Containing Fenofibrate and Microcrystalline Cellulose

Fenofibrate is available by prescription, as an adjunct to diet, for treating adults with very high serum triglyceride levels (high cholesterol). Fenofibrate may be formulated as tablets or capsules that may be taken up to three times a day, preferably with meals. An example is TriCor®, which is currently available in capsules containing 67 mg, 134 mg or 200 mg dosages.

The various components of the example formulations are as follows. Note that these ingredients are standardized and available commercially, and that equivalents are readily known to those of ordinary skill in the art. Micronized fenofibrate has been reduced to a fine powder. Microcrystalline cellulose NF, of this example formulation is Avicel® PH105 (FMC Corp.) and serves as a dispersant. Ac-Di-Sol® (FMC Corp.) is an internally cross-linked carboxymethyl-cellulose (croscarmellose sodium NF) and serves as a disintegrant. Pharmacoat® 606 (Shin-Etsu Chem. Co., Ltd., Tokyo, JP) is hydroxypropyl methyl cellulose, a binding agent. Sodium lauryl sulfate NF (SLS) is a wetting agent. Magnesium stearate NF, serves as a lubricant. The granulation solvent is purified water, USP.

The formulations were prepared according to the following outline:

1. Mix fenofibrate, Avicel® and Ac-Di-Sol® in a high-shear granulator to obtain a well-dispersed fenofibrate and excipient mixture;
2. Dissolve sodium lauryl sulfate and Pharmacoat® in purified water;
3. Wet the granules from step 1 with the solution from step 2;
4. Dry the granules from step 3 in an oven;
5. Mill the dried granules from step 4 through a suitably sized mesh screen with a Fitzpatrick commuting machine;
6. Blend the milled material from step 5 with magnesium stearate in a slant cone blender; and
7. Encapsulate the final blend from step 6 in suitably sized hard gelatin capsules.

Table 1 shows the formulation of 5 preparations comprising fenofibrate and microcrystalline cellulose, prepared as described above.

TABLE 1

Formulations including fenofibrate and microcrystalline cellulose.

| Formulation % W/W | A | B | C | D | E |
|---|---|---|---|---|---|
| Fenofibrate, micronized | 36 | 51.8 | 59.2 | 66.2 | 76.9 |
| Avicel PR 105 | 57.8 | 41.4 | 33.7 | 26.5 | 15.4 |
| SLS | 1.3 | 1.9 | 2.1 | 2.4 | 2.8 |
| Ac-Di-Sol | 4 | 4 | 4 | 4 | 4 |
| Pharmacoat 606 | 0.4 | 0.4 | 0.4 | 0.4 | 0.4 |
| Mg Stearate | 0.5 | 0.5 | 0.5 | 0.5 | 0.5 |
| Avicel/Fenofibrate | 1.6 | 0.8 | 0.6 | 0.4 | 0.2 |

The effect of Avicel®/Fenofibrate ratio on dissolution profiles of fenofibrate was determined by paddle method using a USP Apparatus 2, at 37° C., in water containing 0.5% SLS at 75 rpm. U.S. Pharmacopea (23rd ed. 1995). This dissolution methodology simulates gastric fluid. The amount of fenofibrate dissolved was quantified by standard ultraviolet (UV) spectrophotometry. Alternatively, fenofibrate concentration may be analyzed by standard HPLC techniques. Dissolution profiles of the formulations shown in Table 1 are indicated in Table 2, in which the numbers indicate the percent release over time. These data are also depicted graphically in FIG. 1.

TABLE 2

Dissolution of formulations comprising fenofibrate and microcrystalline cellulose.

| Time (min) | A | B | C | D | E | TriCor ™ |
|---|---|---|---|---|---|---|
| 5 | 41 | 29 | 28 | 19 | 17 | 14 |
| 10 | 84 | 66 | 61 | 51 | 46 | 52 |
| 15 | 95 | 80 | 75 | 65 | 59 | 71 |
| 20 | 96 | 86 | 84 | 73 | 66 | 80 |
| 25 | 95 | 92 | 87 | 77 | 71 | 87 |
| 30 | 95 | 94 | 92 | 82 | 77 | 91 |
| 45 | 95 | 98 | 98 | 91 | 84 | 96 |
| 60 | 95 | 99 | 97 | 93 | 90 | 96 |
|  | (n = 6) | (n = 6) | (n = 6) | (n = 6) | (n = 6) | (n = 6) |

Figure 1:
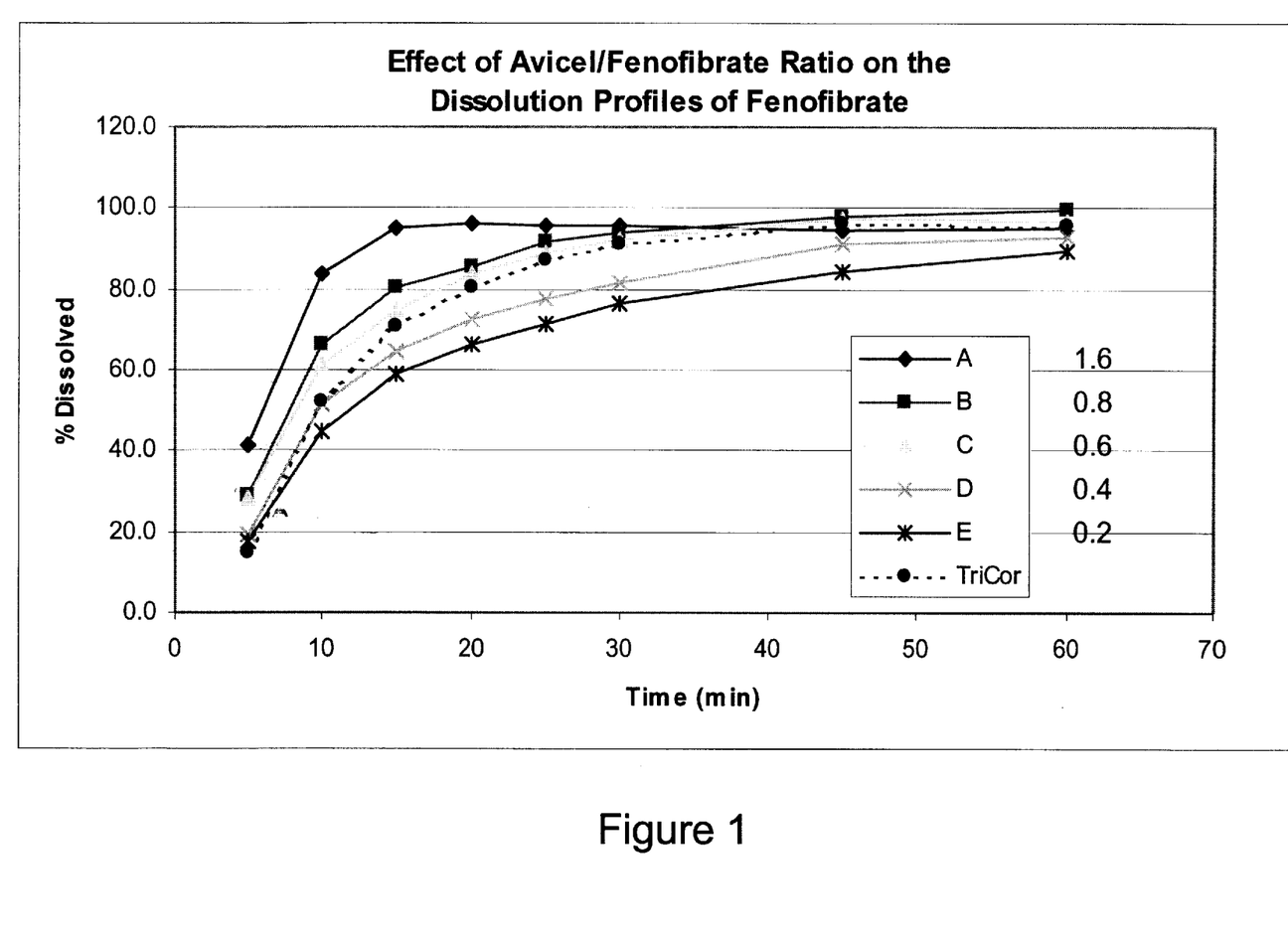
FIG. 1 shows the dissolution profile of five formulations (A through E), comprising fenofibrate and microcrystalline cellulose (Avicel®) compared with the commercially available TriCor™. These formulations are presented in Table 1. The ratios of Avicel® to fenofibrate are 1.6 (A), 0.8 (B), 0.6 (C), 0.4 (D), and 0.2 (E), respectively.

The data presented in Table 2 reflect the dissolution rate of five different ratios of microcrystalline cellulose (Avicel®) to fenofibrate. As FIG. 1 illustrates graphically, ratios of Avicel®/fenofibrate of 1.6 (A), 0.8 (B), and 0.6 (C), dissolve faster than formulations with an Avicel®/fenofibrate ratio of 0.4 (D), 0.2 (E), or the commercially available TriCor®.

Example 2

Formulations Comprising Fenofibrate and Lactose

Formulations comprising fenofibrate and lactose monohydrate were prepared by prior art methods and compared with the commercially available TriCorm®. These formulations and the associated dissolution data, as measured in Example 1, are shown in Tables 3 and 4, respectively.

TABLE 3

Formulations including fenofibrate and lactose monohydrate.

| Formulation % W/W | F | G | H | I |
|---|---|---|---|---|
| Fenofibrate, micronized | 67.34 | 67.34 | 67.34 | 67.34 |
| SLS | 1.01 | 67 | 1.01 | 67 |
| SLS added as | solid | solid | solution | solution |
| Lactose, monohydrate | 22.9 | 17.21 | 22.9 | 17.21 |
| Starch 1500 | 5.05 | 5.05 | 5.05 | 5.05 |
| Crospovidone | 2.02 | 2.02 | 2.02 | 2.02 |
| Mg Stearate | 1.68 | 1.68 | 1.68 | 1.68 |

TABLE 4

Dissolution of formulations comprising fenofibrate and lactose monohydrate.

| Time (min) | F | G | H | I | TriCor ™ |
|---|---|---|---|---|---|
| 5 | 6 | 9 | 8 | 13 | 10 |
| 10 | 18 | 26 | 21 | 34 | 46 |
| 15 | 26 | 44 | 29 | 34 | 65 |
| 20 | 30 | 44 | 36 | 58 | 76 |
| 25 | 35 | 50 | 40 | 64 | 82 |
| 30 | 38 | 56 | 45 | 67 | 86 |
| 45 | 45 | 65 | 54 | 71 | 88 |
| 60 | 50 | 71 | 60 | 74 | 91 |
|  | (n = 6) | (n = 6) | (n = 6) | (n = 6) | (n = 3) |

Figure 2:
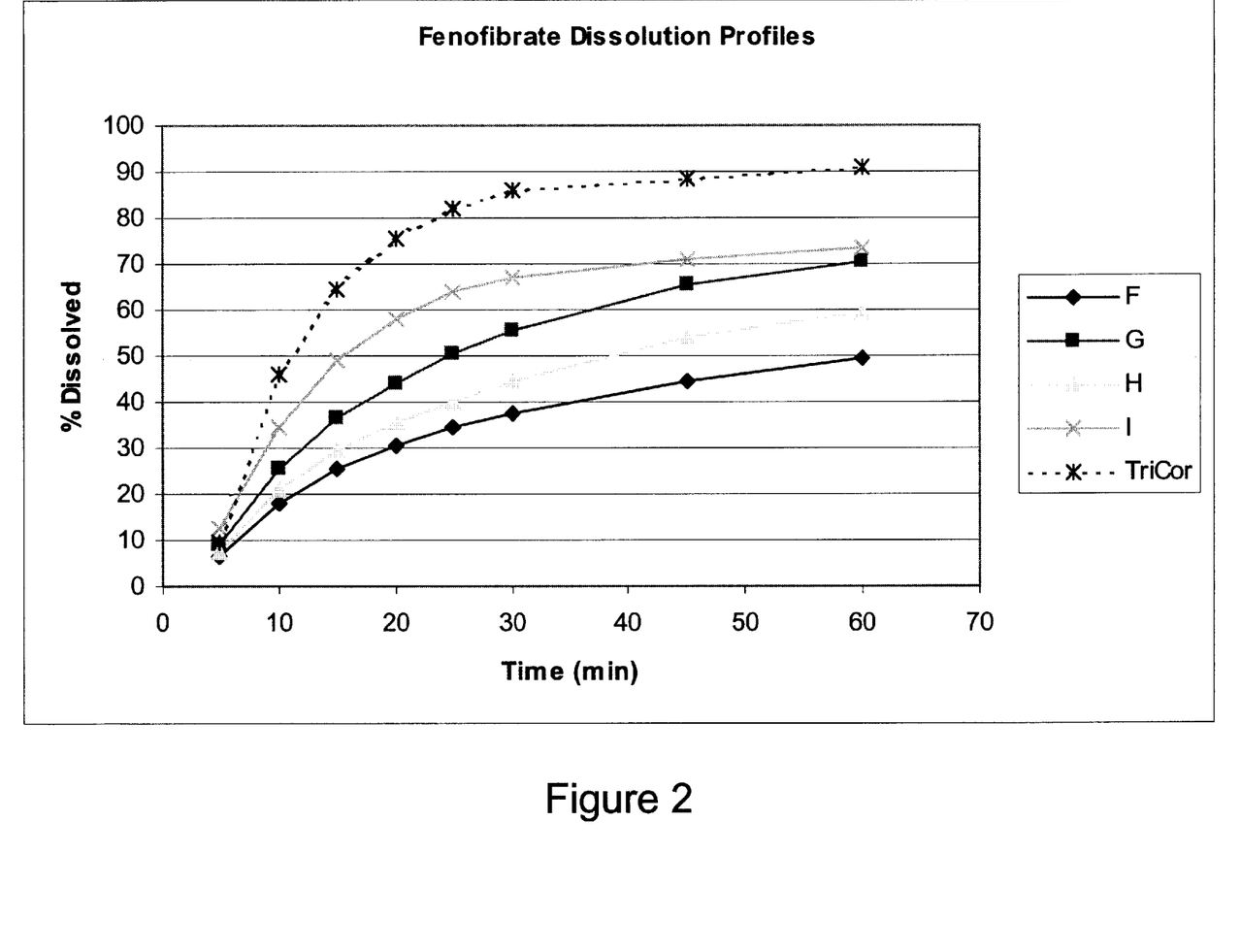
FIG. 2 illustrates the dissolution profiles of four formulations (F through I), comprising fenofibrate and lactose without optimized dispersion, compared to TriCor™. These formulations are detailed in Table 3.

As tabulated in Table 4 and shown graphically in FIG. 2, the formulations prepared by standard mixing techniques, not involving intimate mixing and monitoring to optimize desired dispersion of fenofibrate to lactose, dissolved more slowly than did TriCor™.

Example 3

Formulations Comprising Fenofibrate and Either Lactose or Microcrystalline Cellulose Formulations including fenofibrate and either lactose or microcrystalline cellulose were prepared by intimately mixing the fenofibrate, the inert particles and Ac-Di-Sol® until the fenofibrate was dispersed onto the carrier particles such that no fenofibrate aggregates were visible upon microscopic inspection. The lactose, anhydrous, was milled by passage through a #60 mesh screen prior to the preparation of the batch, which was otherwise carried out as in Example 1.

The formulations for these preparations are shown in Table 5. The dissolution profiles were measured using paddle dissolution at 37° C., in 1% SLS in water, at 75% rpm. U.S. Pharmacopea (23 ed. 1995), using a UV monitor. These data are tabulated in Table 6, and shown graphically in FIG. 3.

TABLE 5

Formulations including fenofibrate and either microcrystalline cellulose or anhydrous lactose.

| Formulation % W/W | J | K | L | M |
|---|---|---|---|---|
| Fenofibrate, micronized | 44.67 | 44.67 | 33.5 | 33.5 |
| Avicel PH105 | 50.43 | 0 | 61.6 | 0 |
| Lactose, anh. (milled) | 0 | 50.43 | 0 | 61.6 |
| SLS | 2 | 2 | 2 | 2 |
| Crospovidone | 2 | 2 | 2 | 2 |
| Mg Stearate | 0.5 | 0.5 | 0.5 | 0.5 |
| Pharmacoat 606 | 0.4 | 0.4 | 0.4 | 0.4 |

TABLE 6

Dissolution of formulations comprising fenofibrate and either microcrystalline cellulose or anhydrous lactose.

| Time (min) | J | K | L | M | TriCor ™ |
|---|---|---|---|---|---|
| 5 | 24 | 24 | 21 | 20 | 9 |
| 10 | 54 | 55 | 72 | 53 | 60 |
| 15 | 68 | 71 | 82 | 76 | 79 |
| 20 | 73 | 78 | 84 | 82 | 85 |
| 30 | 81 | 82 | 88 | 88 | 88 |
| 45 | 84 | 84 | 90 | 89 | 90 |
| 60 | 84 | 84 | 92 | 90 | 90 |
|  | (n = 4) | (n = 4) | (n = 4) | (n = 4) | (n = 8) |

Figure 3:
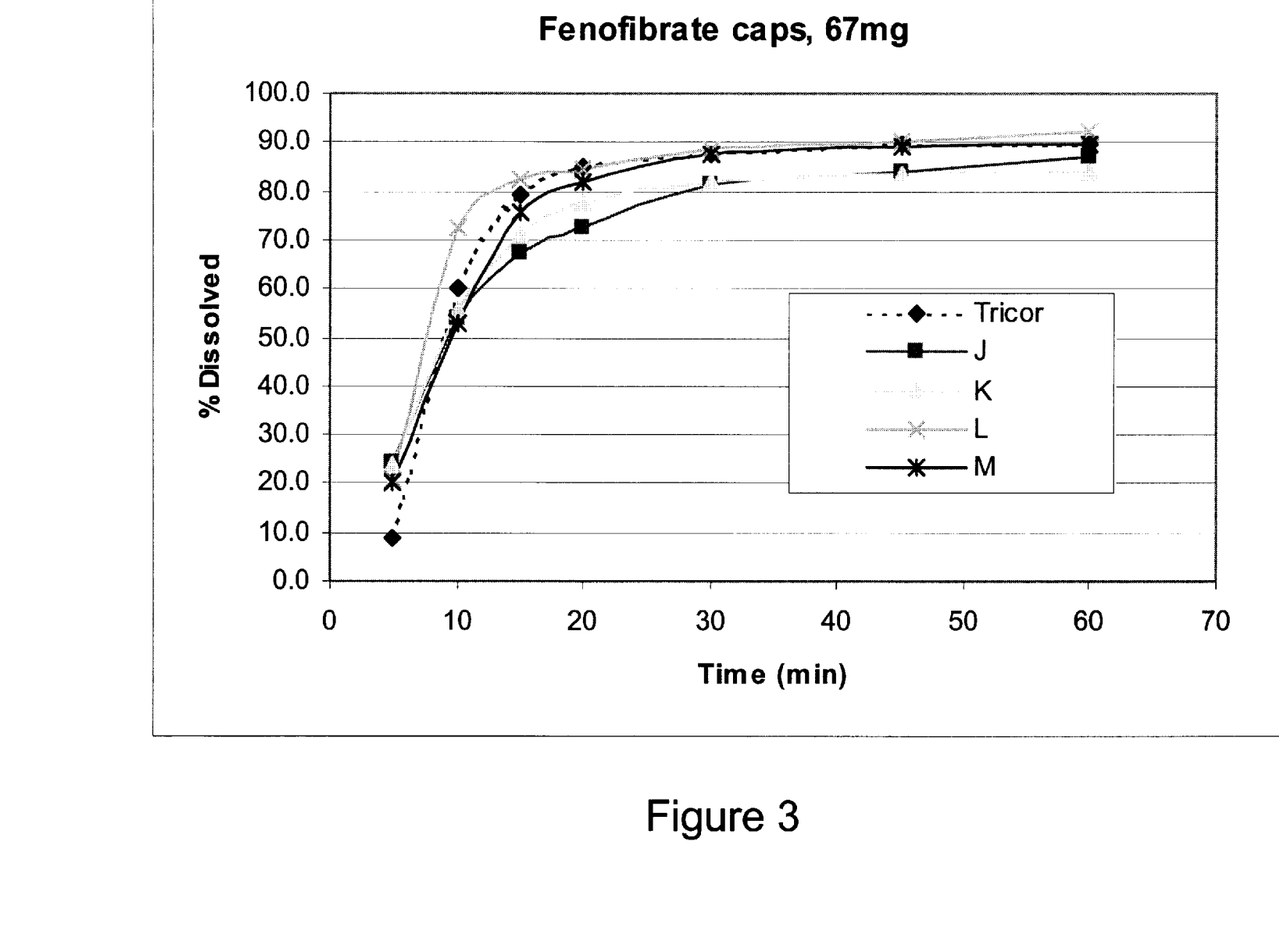
FIG. 3 shows the dissolution profiles of four formulations, two comprising microcrystalline cellulose (J) and (L) or lactose (K) and (M) prepared with optimized dispersion. These formulations are detailed in Table 5.

The data presented in Table 6 and FIG. 3 indicate that inert substrates of suitable particle size may be intimately mixed with a hydrophobic active ingredient and monitored to maximize dispersion of the active drug to the minute particles. Optimizing dispersion greatly improves the drug's dissolution.

Example 4

Bioavailability of Fenofibrate-containing Formulations

Several formulations comprising fenofibrate and microcrystalline cellulose were prepared and tested in patients. The formulations shown in Table 7 were prepared as outlined in Example 1, except that PVP 29/32 (polyvinylpyrrolidone) was added as an additional binding agent. Patients fasted over night prior to dosing. Plasma samples were then taken and analyzed for the concentration of fenofibric acid, fenofibrate's active metabolite. These data are expressed as $C_{max}$, the maximum amount of fenofibric acid in the blood plasma, and as AUC, the area under the plasma concentration time curve. Shargel & Yu, Applied Biopharmaceutics and Pharmacokinetics ch. 10 (3rd Ed. 1996).

TABLE 7

Formulations comprising fenofibrate and microcrystalline cellulose.

| Formulation % W/W | N | O | P | Q | R | S | T | U |
|---|---|---|---|---|---|---|---|---|
| Fenofibrate, micronized | 55.8 | 67.0 | 33.5 | 33.5 | 59.2 | 71.2 | 83.8 | 71.0 |
| Avicel PH 105 | 31.7 | 23.5 | 53.6 | 48.6 | 33.7 | 21.4 | 8.4 | 7.1 |
| PVP 29/32 | 5.0 | 5.0 | 0.0 | 0.0 | 0.0 | 0.0 | 0.0 | 0.0 |
| Pharmacoat 606 | 0.0 | 0.0 | 0.4 | 5.4 | 0.4 | 0.4 | 0.4 | 0.4 |
| Sodium Lauryl Sulfate | 2.0 | 2.0 | 8.0 | 8.0 | 2.1 | 2.6 | 3.0 | 17.0 |
| Crospovidone | 5.0 | 2.0 | 0.0 | 0.0 | 0.0 | 0.0 | 0.0 | 0.0 |
| Ac-Di-Sol | 0.0 | 0.0 | 4.0 | 4.0 | 4.0 | 4.0 | 4.0 | 4.0 |
| Mg Stearate | 0.5 | 0.5 | 0.5 | 0.5 | 0.5 | 0.5 | 0.5 | 0.5 |
| Avicel/fenofibrate | 0.6 | 0.4 | 1.6 | 1.5 | 0.6 | 0.3 | 0.1 | 0.1 |
| in vivo bioavailability data (test/ref*). fasting | | | | | | | | |
| Cmax | 0.705 | 0.562 | 1.697 | 1.745 | 1.013 | 0.896 | 1.079 | 0.899 |
| AUC | 0.858 | 0.718 | 1.615 | 1.602 | 1.089 | 0.986 | 1.112 | 0.816 |
| no. of subjects | 12 | 12 | 12 | 12 | 11 | 11 | 7 | 7 |

*Reference is Tricor ™ 67 mg capsules.

TABLE 8

Dissolution and Bioavailability of Fenofibrate/Microcrystalline Cellulose Formulations.

| Time (min.) | N | O | P | Q | TriCor ™ |
|---|---|---|---|---|---|
| 5 | 12 | 3 | 38 | 21 | 14 |
| 10 | 37 | 14 | 81 | 79 | 52 |
| 15 | 53 | 23 | 90 | 92 | 71 |
| 20 | 67 | 31 | 92 | 94 | 80 |
| 25 | 77 | 37 | 93 | 95 | 87 |
| 30 | 85 | 42 | 95 | 96 | 91 |
| 45 | 94 | 55 | 95 | 95 | 96 |
| 60 | 98 | 64 | 90 | 89 | 96 |
|  | (n = 6) | (n = 6) | (n = 6) | (n = 6) | (n = 6) |
| Avicel/fenofibrate | 0.6 | 0.4 | 1.6 | 1.5 |  |
| Cmax | 0.705 | 0.562 | 1.697 | 1.745 |  |
| AUC | 0.858 | 0.718 | 1.615 | 1.602 |  |
| no. of subjects | 12 | 12 | 12 | 12 |  |

TABLE 9

Dissolution and Bioavailability of Fenofibrate/Microcrystalline Cellulose Formulations.

| Time (min.) | R | S | T | U | TriCor ™ |
|---|---|---|---|---|---|
| 5 | 20 | 21 | 17 | 9 | 10 |
| 10 | 59 | 57 | 48 | 42 | 49 |
| 15 | 77 | 73 | 62 | 58 | 70 |
| 20 | 86 | 82 | 69 | 66 | 79 |
| 25 | 91 | 88 | 74 | 72 | 84 |
| 30 | 93 | 90 | 77 | 77 | 87 |
| 45 | 95 | 98 | 86 | 87 | 92 |
| 60 | 95 | 100 | 92 | 94 | 94 |
|  | (n = 18) | (n = 6) | (n = 6) | (n = 6) | (n = 1 2) |
| Avicel/fenofibrate | 0.6 | 0.3 | 0.1 | 0.1 |  |
| Cmax | 1.013 | 0.896 | 1.079 | 0.899 |  |
| AUC | 1.089 | 0.986 | 1.112 | 0.816 |  |
| no. of subjects | 11 | 11 | 7 | 7 |  |

Figure 4:
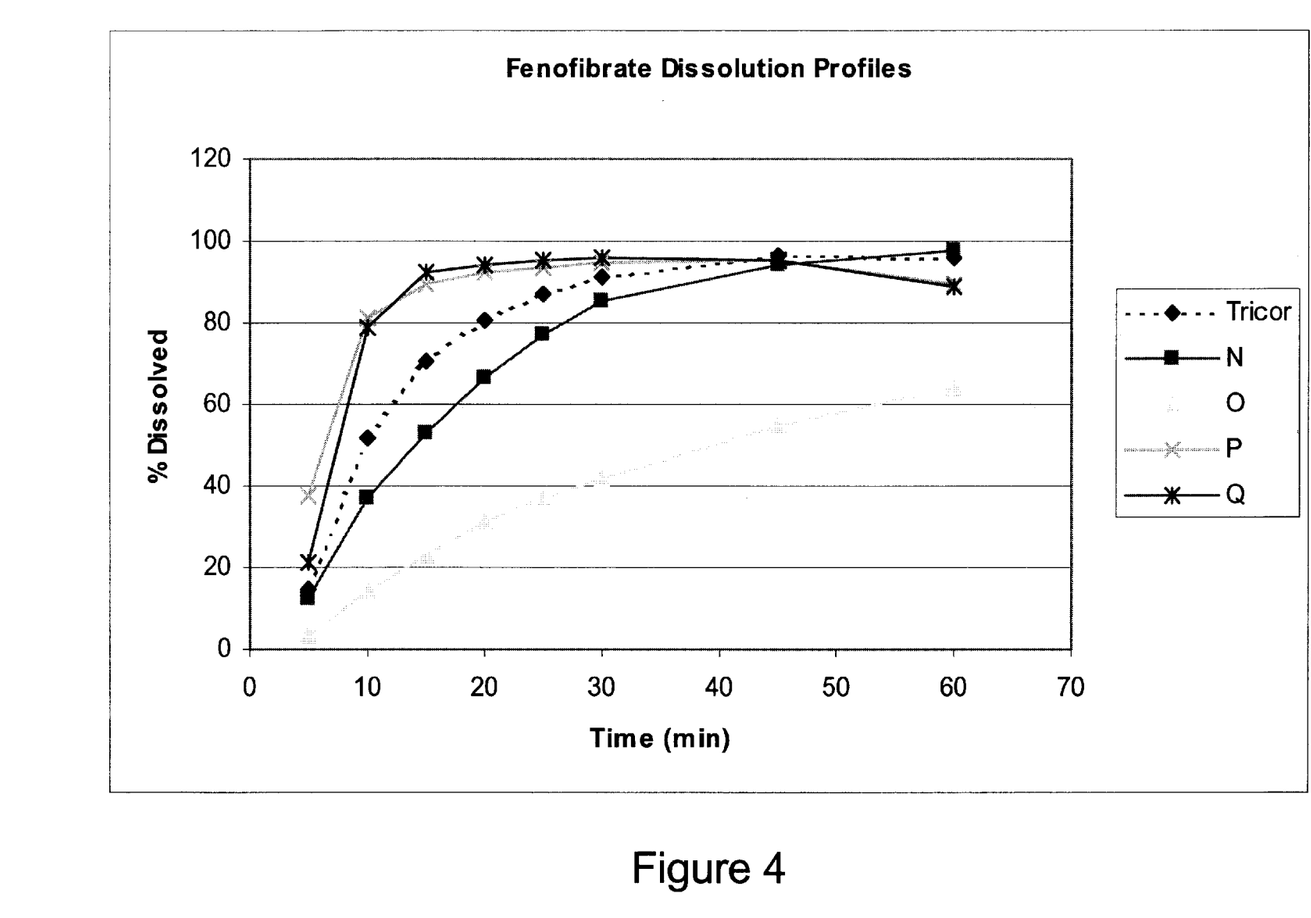
FIG. 4 illustrates the dissolution profile of four formulations (N, O, P, and Q), comprising fenofibrate and microcrystalline cellulose, compared with TriCor™. These formulations are detailed in Table 7. The in vivo bioavailability data related to these formulations are presented in Table 7 as well.
Figure 5:
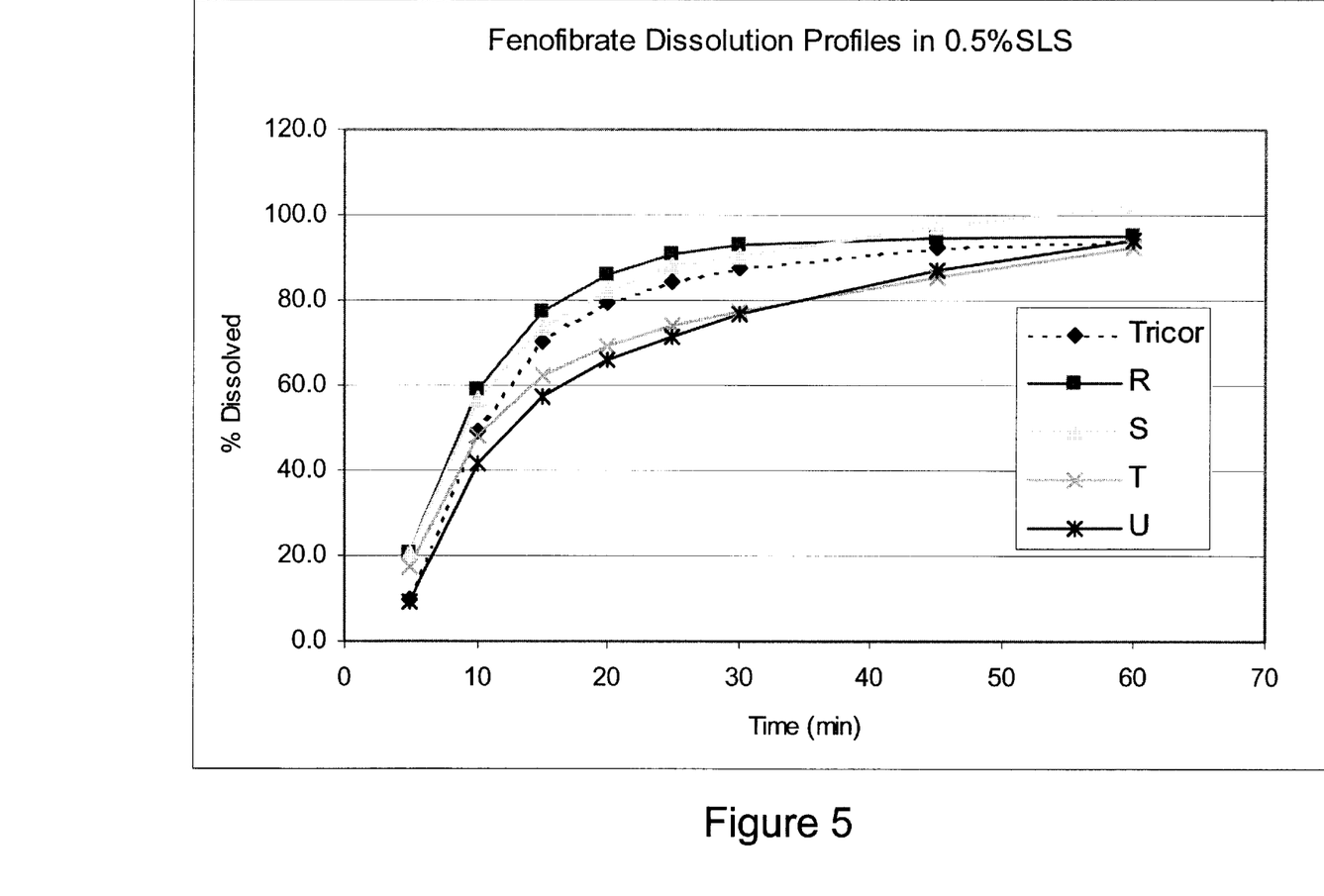
FIG. 5 illustrates the dissolution profile of four formulations (R, S, T, and U), comprising fenofibrate and microcrystalline cellulose, compared to TriCor™. These formulations are detailed in Table 7. The in vivo data related to these formulations are also presented in Table 7.

The data on bioavailability in Tables 7, 8 and 9 indicate that the bioavailability of fenofibrate can be tailored both by varying the ratio of inert carrier to fenofibrate, and by optimizing the dispersion, in processing, to achieve the desired dissolution (FIGS. 4 and 5) of the active ingredient to inert substrate. This allows for the control and enhancement of the drug's bioavailability upon ingestion.

Example 5

Bioavailability of a Formulation Containing 67 mg Fenofibrate

Formulation P, as described in Example 4 was used in a comparative bioavailability study in 12 subjects. Formulation P, 67 mg fenofibrate, was compared with a 67 mg dose of Tricor™. Patients fasted over night prior to drug administration. Plasma samples were then taken at dosing, and every hour for twelve hours after dosing, and then at sixteen and twenty-four hours after dosing, and analyzed for the ng/ml concentration of fenofibric acid, fenofibrate's active metabolite. Table 10 depicts the average concentration in ng/ml of fenofibric acid in blood plasma. Additionally, this data is reflected graphically in FIG. 6.

TABLE 10

Comparative Bioavailability of Fenofibrate.

| Time (hours) | Formulation P, 67 mg | Tricor, 67 mg |
|---|---|---|
| 0 | 19.9 ng/ml | 20.1 ng/ml |
| 1 | 217.6 | 89.2 |
| 2 | 620.3 | 296.0 |
| 3 | na | na |
| 4 | 1112.0 | 652.7 |
| 5 | 1240.2 | 715.0 |
| 6 | 1329.4 | 771.5 |
| 7 | 1311.7 | 754.2 |
| 8 | 1256.1 | 736.4 |
| 9 | 1166.9 | 747.4 |
| 10 | 1159.8 | 716.2 |
| 12 | 1110.5 | 692.8 |
| 16 | 914.5 | 602.0 |
| 24 | 815.9 | 555.4 |

Figure 6:
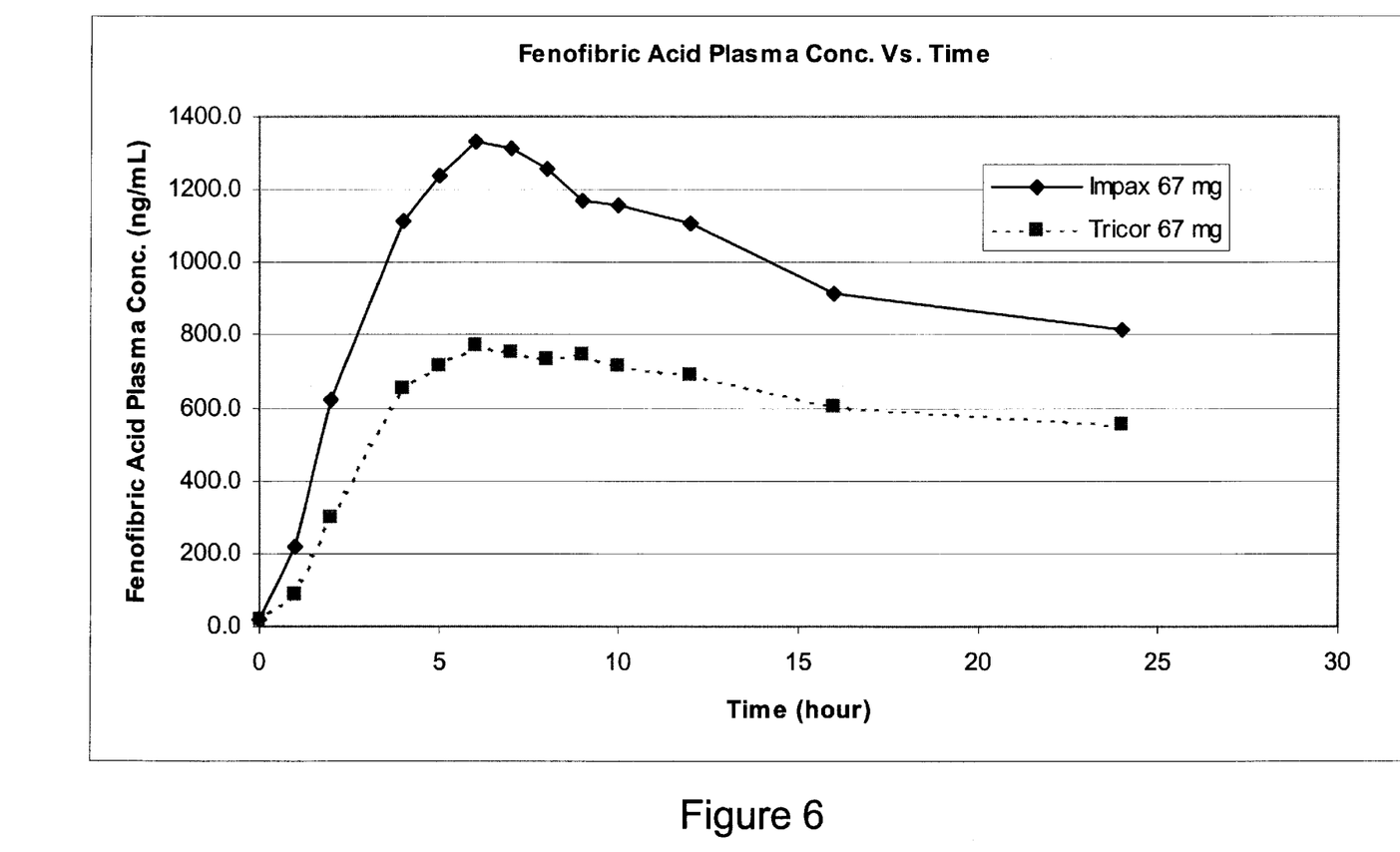
FIG. 6 shows the blood plasma levels of fenofibric acid over a twenty-four hour period following ingestion of a formulation P, comprising 67 mg fenofibrate and microcrystalline cellulose.

Table 10 and FIG. 6 illustrate that the dispersion of a hydrophobic drug with a minute particle may be optimized to improve the bioavailability of the hydrophobic drug. Indeed, these data show that the same amount of active ingredient may be dispersed in a preparation as taught herein to achieve better bioavailability compared to standard preparations.

Example 6

Dissolution of Capsules Comprising 67 mg or 200 mg Fenofibrate

A preparation comprising 67 mg fenofibrate and microscrystalline cellulose was prepared as in Example 4, formulation R. The dissolution profiles were measured using paddle dissolution at 37° C., in 1% SLS in water, at 75 rpm. U.S. Pharmacopea (23 ed. 1995). The amount of fenofibrate in each time sample was determined by HPLC. Formulation R was compared with TriCor™, as shown in Table 11, for percent of fenofibrate dissolved over time:

TABLE 11

Dissolution of 67 mg Fenofibrate Capsules.

| | % Dissolved by Time (Minutes) | | | | | |
|---|---|---|---|---|---|---|
| | 5 | 10 | 20 | 30 | 45 | 60 |
| Formulation R | 45.2 | 64.4 | 81.7 | 87.3 | 93.7 | 97.2 |
| TriCor | 35.4 | 63.1 | 79.8 | 85.3 | 89.9 | 93.4 |

The data in Table 11 indicate that the 67 mg formulation R, prepared with optimized dispersion dissolves more quickly upon contact with aqueous solution containing a surfactant than does a known preparation.

Another preparation of formulation R, comprising 200 mg fenofibrate, was prepared as described above. The dissolution profiles were measured using paddle dissolution at 37° C., in 1% SLS in water, at 75 rpm. U.S. Pharmacopea (23 ed. 1995). The amount of fenofibrate in each time sample was determined by HPLC. Table 12 illustrates that this preparation exhibited immediate release upon exposure to an aqueous solution containing a surfactant, dispersing in the first 5 minutes more rapidly than a known preparation.

TABLE 12

Dissolution of 200 mg Fenofibrate Capsules.

| | % Dissolved by Time (Minutes) | | | | | |
|---|---|---|---|---|---|---|
| | 5 | 10 | 20 | 30 | 45 | 60 |
| Formulation R | 36.7 | 52.6 | 64.6 | 70.0 | 76.2 | 80.5 |
| TriCor | 12.9 | 63.1 | 77.1 | 82.8 | 88.2 | 90.9 |

Those skilled in the art will find it apparent that various modifications and variations can be made to the formulations of this invention. Thus, the present invention is intended to cover such modifications and variations, provided that they come within the scope of the appended claims and their equivalents.

The disclosures of all publications cited above are expressly incorporated by reference in their entireties to the same extent as if each were incorporated by reference individually.

We claim:

1. A drug delivery system comprising micronized fenofibrate or a pharmaceutically acceptable salt thereof and an inert substrate of suitable particle size, selected from microcrystalline cellulose or lactose, which when orally administered as a single 67 mg dose in adults maintains post ingestion blood plasma levels of fenofibric acid of:
   at least about 100 mg/ml at one hour;
   at least about 350 mg/ml at two hours;
   at least about 750 mg/ml at four hours;
   at least about 850 mg/ml at five hours; and
   at least about 650 mg/ml at twenty-four hours.

2. The drug delivery system of claim 1, wherein said inert substrate particle has a mean particle size range of between about 1 micron and about 500 microns.

3. The delivery system of claim 2, wherein said inert substrate particle has a mean particle size of less than about 50 microns.

4. The drug delivery system of claim 1, wherein the ratio of said inert substrate particle to said hydrophobic drug is from about 0.1 to about 10.0.

5. The drug delivery system of claim 4, wherein the ratio of said inert substrate particle to said hydrophobic drug is from about 0.1 to about 4.0.

6. The drug delivery system of claim 5, wherein the ratio of said inert substrate particle to said hydrophobic drug is from about 0.3 to about 2.0.

7. The drug delivery system of claim 1, wherein said system is in solid form.

8. The drug delivery system of claim 7, wherein said system is in a liquid form.

9. The drug delivery system of claim 7, wherein said solid drug delivery form is a capsule.

10. The drug delivery system of claim 7, wherein said solid drug delivery form is a tablet.

11. The drug delivery system of claim 7, wherein said solid drug delivery form is a powder.

12. The drug delivery system of claim 1, which after oral administration of a single 67 mg dose of said drug delivery system in adults produces blood plasma levels of fenofibric acid and ranging between 19.9 to 1329.4 mg/ml.

13. The drug delivery system of claim 1 which after oral administration of a single 67 mg dose of said drug delivery system in adults maintains post ingestion blood plasma levels of fenofibric acid of:
   at least about 200 ng/ml at one hour;
   at least about 600 ng/ml at two hours;
   at least about 1000 ng/ml at four hours;
   at least about 1200 ng/ml at five hours; and
   at least about 800 ng/ml at twenty-four hours.

14. The drug delivery system of claim 1, wherein said fenofibrate exhibits the following in vitro dissolution profile when measured in a type 2 paddle dissolution apparatus at 37° C. in aqueous solution containing 0.5% sodium lauryl sulfate at 75 rpm:
   a) from about 40% to 50% of the total fenofibrate is released after five minutes of measurement in said apparatus;
   b) from about 60% to 75% of the total fenofibrate is released after ten minutes of measurement in said apparatus; and
   c) no less than about 75% of the total fenofibrate is released after twenty minutes of measurement in said apparatus.

15. The drug delivery system of claim 1, wherein at least about 36% of fenofibrate dissolves in the first five minutes after being placed in a type 2 paddle dissolution apparatus at 37° C. in aqueous solution containing 0.5% sodium lauryl sulfate at 75 rpm.

16. The drug delivery system of claim 1, wherein said system contains 67 mg fenofibrate.

17. The drug delivery system of claim 16, wherein said fenofibrate exhibits the following in vitro dissolution profile when measured in a type 2 paddle dissolution apparatus at 37° C. in aqueous solution containing 0.5% sodium lauryl sulfate at 75 rpm:
   a) from about 40% to 50% of the total fenofibrate is released after five minutes of measurement in said apparatus;
   b) from about 64% to 75% of the total fenofibrate is released after ten minutes of measurement in said apparatus; and
   c) no less than about 80% of the total fenofibrate is released after twenty minutes of measurement in said apparatus.

18. The drug delivery system of claim 1, wherein said system contains 200 mg fenofibrate.

19. The drug delivery system of claim 18, wherein said fenofibrate exhibits the following in vitro dissolution profile when measured in a type 2 paddle dissolution apparatus at 37° C. in aqueous solution containing 0.5% sodium lauryl sulfate at 75 rpm a) from about 20% to 50% of the total fenofibrate is released after five minutes of measurement in said apparatus;

b) from about 50% to 64% of the total fenofibrate is released after ten minutes of measurement in said apparatus; and c) no less than about 64% of the total fenofibrate is released after twenty minutes of measurement in said apparatus.

\* \* \* \* \*

UNITED STATES PATENT AND TRADEMARK OFFICE
CERTIFICATE OF CORRECTION

PATENT NO. : 6,531,158 B1 Page 1 of 1
APPLICATION NO. : 09/635234
DATED : March 11, 2003
INVENTOR(S) : Ching-Ling Teng, Charles Hsiao and Joshua Gatts It is certified that error appears in the above-identified patent and that said Letters Patent is hereby corrected as shown below:

Replace the term "mg/ml" in Column 11, lines 54-58 (Claim 1) and in Column 12, line 20 (Claim 12) with the term "ng/ml".

Signed and Sealed this

Eighteenth Day of May, 2010

David J. Kappos
*Director of the United States Patent and Trademark Office*